(12) United States Patent
Taranekar et al.

(10) Patent No.: US 9,591,979 B2
(45) Date of Patent: Mar. 14, 2017

(54) POLYMER NANO-COMPOSITES AS DRY SENSOR MATERIAL FOR BIOSIGNAL SENSING

(71) Applicant: Cleveland Medical Polymers, Inc., Cleveland, OH (US)

(72) Inventors: Prasad Taranekar, Cleveland, OH (US); Arunkumar Venkatesan, Twinsburg, OH (US); Nishant Negandhi, Medina, OH (US); Asis Banerjie, Medina, OH (US)

(73) Assignee: Cleveland Medical Polymers, Inc, Cleveland, OH (US)

( * ) Notice: Subject to any disclaimer, the term of this patent is extended or adjusted under 35 U.S.C. 154(b) by 680 days.

(21) Appl. No.: 14/076,652

(22) Filed: Nov. 11, 2013

(65) Prior Publication Data

US 2014/0066740 A1   Mar. 6, 2014

Related U.S. Application Data

(62) Division of application No. 13/033,314, filed on Feb. 23, 2011, now Pat. No. 8,608,984.

(Continued)

(51) Int. Cl.
*A61B 5/04*   (2006.01)
*A61B 5/0408*   (2006.01)
(Continued)

(52) U.S. Cl.
CPC .......... *A61B 5/0408* (2013.01); *A61B 5/6891* (2013.01); *H01B 1/24* (2013.01); *A61B 5/6804* (2013.01); *A61B 2562/06* (2013.01)

(58) Field of Classification Search
CPC . A61B 5/04087; A61B 2562/125; A61B 5/04; A61B 2562/046; A61B 5/053;
(Continued)

(56) References Cited

U.S. PATENT DOCUMENTS

| | | | |
|---|---|---|---|
| 4,865,039 A | 9/1989 | Dunseath, Jr. et al. | ...... 600/410 |
| 5,427,096 A | 6/1995 | Bogusiewicz et al. | |

(Continued)

FOREIGN PATENT DOCUMENTS

| | | |
|---|---|---|
| JP | 2013 111361 A | 6/2013 |
| KR | 2013 0020429 A | 2/2013 |

(Continued)

OTHER PUBLICATIONS

Ju-Yeoul Baek et al, "Flexible polymeric dry electrodes for the long term monitoring of ECG", Sensors and Acuators, A 143 (2008), pp. 423-429.

(Continued)

*Primary Examiner* — Joseph Stoklosa
*Assistant Examiner* — Brian M Antiskay
(74) *Attorney, Agent, or Firm* — Alvin T. Rockhill

(57) ABSTRACT

The multifunctional polymer nano-composite sensor system for detecting various biosignals, such as EKG, includes (1) a polymer nano-composite sensor material that is flexible, elastic, soft, and conductive, (2) a sensor material fabricated into a desired shape or form, and (3) a signal capturing interface for collecting, transmitting and processing the signals. The present invention more specifically reveals a multi-functional nano-composite sensor for detecting biologically generated electrical signals which is comprised of a polymeric composition having an electrically conductive wire embedded therein, wherein the polymeric composition has a dispersion phase and a dispersed phase, wherein the dispersion phase is comprised of a thermoplastic polymer or a thermoset polymer, wherein the dispersed phase includes an electrically conductive filler, wherein the polymeric composition is gel-free, and wherein the electrically conductive wire is adapted for conveying an electrical signal to a signal processing device.

16 Claims, 14 Drawing Sheets

Related U.S. Application Data

(60) Provisional application No. 61/307,038, filed on Feb. 23, 2010.

(51) Int. Cl.
 *H01B 1/24* (2006.01)
 *A61B 5/00* (2006.01)

(58) Field of Classification Search
 CPC ... A61B 5/6869; A61B 5/0006; A61B 5/0205; A61B 5/0416; A61B 5/6804; A61B 5/6824; A61B 5/683; A61B 5/72; A61B 5/0402; A61B 5/681; A61B 5/6831
 USPC ............ 600/372, 382–384, 386, 388–393, 600/395–397, 508–509
 See application file for complete search history.

(56) References Cited

U.S. PATENT DOCUMENTS

| | | |
|---|---|---|
| 6,510,333 B1 | 1/2003 | Licata et al. .................. 600/383 |
| 6,516,289 B2 | 2/2003 | David ............................ 702/189 |
| 6,970,731 B1 | 11/2005 | Jayaraman et al. ........... 600/388 |
| 7,032,301 B1 | 4/2006 | Schmidt et al. ................ 29/825 |
| 8,050,733 B2 | 11/2011 | Rytky ............................ 600/388 |
| 8,165,654 B2 | 4/2012 | Tang et al. .................... 600/388 |
| 8,340,740 B2 | 12/2012 | Holzer et al. ................. 600/388 |
| 8,608,984 B1 | 12/2013 | Taranekar |
| 2003/0113531 A1 | 6/2003 | Hajmrle |
| 2003/0173550 A1 | 9/2003 | Fox et al. ..................... 252/500 |
| 2004/0064026 A1* | 4/2004 | Perrault ............. A61B 5/04087 600/391 |
| 2007/0078324 A1* | 4/2007 | Wijisiriwardana A41D 13/1281 600/386 |
| 2008/0091097 A1 | 4/2008 | Linti |
| 2010/0209599 A1 | 8/2010 | Van Veen et al. ......... 427/126.1 |
| 2010/0268056 A1* | 10/2010 | Picard .................. A61B 5/0531 600/388 |
| 2011/0021899 A1 | 1/2011 | Arps et al. |
| 2011/0257504 A1* | 10/2011 | Hendricks ............ A61B 5/0408 600/395 |
| 2012/0073388 A1 | 3/2012 | Chibante .................. 73/862.627 |
| 2012/0177934 A1 | 7/2012 | Vogel et al. ................... 428/457 |
| 2012/0266685 A1 | 10/2012 | Choi et al. ....................... 73/774 |
| 2013/0150689 A1 | 6/2013 | Shaw-Klein |

FOREIGN PATENT DOCUMENTS

| | | |
|---|---|---|
| WO | WO 84/02423 A1 | 6/1984 |
| WO | WO 2012/140079 | 10/2012 |

OTHER PUBLICATIONS

Rupali Gangopadhyay et al, "Conducting Polymer Nanocomposites: A Brief Overview", Chem. Mater. vol. 12, No. 3 (2000), pa 608-622.

Hofffman, K.P., "Flexible dry surface-electrodes for ECG long term-monitoring," Engineering in Medicine and Biology Society, (2007), pp. 5739-5742.

* cited by examiner

| Exp # | Lab ID | Material Description | Correlation | Qualitative | Signal |
|---|---|---|---|---|---|
| 1 | CP412x1 | Polyac PA757 + 15% CNT (C100) | N/A | N/A | N/A |
| 2 | CP413x2 | Polyac PA757 + EMA + 13% CNT (Nanocyl) | N/A | N/A | N/A |
| 3 | CP416x1 | Polyac PA757 + 15% CNT (baytubes) | N/A | N/A | N/A |
| 4 | CP551x2 | EMA + 8% CNT (C100) | N/A | N/A | Flat signal |
| 5 | CP551x1 | EMA + 12% CNT (C100) | 53.38 | Bad | |
| 6 | MB121x3 | EMA + 25% CNT (C100) | 97.38 | Very good | |

FIG-10

| Exp # | Lab ID | Material Description | Correlation | Qualitative | Signal |
|---|---|---|---|---|---|
| 7 | CP557x2 | EMA + 12% SWeNT | 96.53 | Good | |
| 8 | CP556x1 | EMA + 12% CB | N/A | N/A | Flat signal |
| 9 | CP556x3 | EMA + 25% CB | 99.75 | Excellent | |
| 10 | CP552x1 | EMA + 6% CNT (C100) + 6% CB | N/A | N/A | Flat signal |
| 11 | CP552x3 | EMA + 3% CNT (C100) + 18% CB | 78.39 | Bad | |

FIG-10A

| Exp # | Lab ID | Material Description | Correlation | Qualitative | Signal |
|---|---|---|---|---|---|
| 12 | CP552x5 | EMA + 6% CNT (C100) + 24% CB | 66.08 | Bad | |
| 13 | CP479x5 | Hytrel + 8% SWeNT | 96.27 | Good | |
| 14 | CP478x5 | LLDPE (Westlake LF2018AB) + 8% SWeNT | 85.7 | Average | |

FIG-10B

| Exp # | Lab ID | Material Description | Correlation | Qualitative | Signal |
|---|---|---|---|---|---|
| 15 | CP476x5 | PP (3155) + 8% SWeNT | 85.11 | Average | |
| 16 | CP536x3 | Sibstar 103T + 18% CB | N/A | N/A | Flat signal |
| 17 | CP536x2 | Sibstar 103T + 18% CB + 3% CNT (Cnano) | 96.28 | Good | |
| 18 | CP536x1 | Sibstar 103T + 6% CNT (Cnano) | N/A | N/A | Flat signal |
| 19 | CP538x1 | TPU (PearlThane 15N70) + 6% CNT (Cnano) | 87.17 | Average | |

FIG-10C

| Exp # | Lab ID | Material Description | Correlation | Correlation Qualitative | Signal |
|---|---|---|---|---|---|
| 23 | CP534x2 | TPU (PearlThane 16N80) + 18% CB + 3% CNT (C100) | 95.01 | Good | |
| 24 | CP554x4 | TPU (PearlThane 16N80) + 6% CNT (C100) + 18% CB | 98.14 | Very good | |
| 25 | CP539x1 | TPU (PearlThane15N70) + Sibstar 073T + 6% CNT (Cnano) | 99.69 | Excellent | |

FIG-10E

| Exp # | Lab ID | Material Description | Correlation | Qualitative | Signal |
|---|---|---|---|---|---|
| 26 | CP539x3 | TPU (PearlThane15N70) + Sibstar 073T + 6% CNT (Cnano) + 18% CB | 99.37 | Excellent | |
| 27 | CP539x2 | TPU (PearlThane15N70) + Sibstar 073T + 6% CNT (Cnano) + 2% CB | 99.94 | Excellent | |
| 28 | CP425R1x5 | Pebax(40%) + EMA(6%) + Skygreen(30%) + 10% CNT (C100) | N/A | N/A | N/A |

FIG-10F

POLYMER NANO-COMPOSITES AS DRY SENSOR MATERIAL FOR BIOSIGNAL SENSING

This application is a divisional of U.S. patent application Ser. No. 13/033,314, filed on Feb. 23, 2011, which claims the benefit of United States Provisional Patent Application Ser. No. 61/307,038, filed on Feb. 23, 2010. The teachings of U.S. patent application Ser. No. 13/033,314 and U.S. Provisional Patent Application Ser. No. 61/307,038 are incorporated herein by reference in their entirety.

BACKGROUND OF THE INVENTION

The use of electrodes to sense and measure bio-potential signals is widely practiced in the medical field as part of the various diagnostic tools like electrocardiography (ECG/EKG) for monitoring heart function and electroencephalography (EEG) for studying brain activity and the like. The prior art for these techniques is to use a metal electrode which is in contact with its ionic form through a gel-bound electrolyte which then contacts the skin. A commonly used system of this type is the "wet" electrode which is typically a Ag/AgCl electrode. These systems suffer from many disadvantages documented in literature such as the requirement of skin preparation including removal of hairs by shaving, and removal of the Stratum Corneum by scrubbing. Furthermore, wet electrodes commenly cause skin irritation in persons with sensitive skin.

Previous work on biopotential sensors has been done by Licata and Mitchell on the use of soft elastomeric bristles filled with a conductive liquid as a biopotential sensor (see U.S. Pat. No. 6,510,333). The technique of U.S. Pat. No. 6,510,333 art does not require preparation of the skin, however it does require liquid to be in the bristles and also recommends an abrasive scrubbing of the skin in order to eliminate resistance from the surface of the skin. The bristles also require refilling throughout their lifetime which can be an added inconvenience to the user.

Previous work on dry electrodes has been done by Dunseath Jr. (see U.S. Pat. No. 4,865,039) on a dry electrode assembly. However, the maximum allowed volume resistivity for these electrodes to be effective it reported to be 200KΩ-cm using a graphite-loaded polyurethane foam material. Moreover, this assembly requires a lead amplifier for improving the signal strength of the bio-potentials.

Previous work on dry electrodes has also been done by Schmidt, Lisy, Skebe, and Prince from Orbital Research Inc. (U.S. Pat. No. 7,032,301) on a dry physiological recording electrode that does not require any skin preparation. This prior art assembly requires constant contact with the skin. To ensure constant contact the assembly pierces the skin in order to obtain a biopotential signal which can cause pain and discomfort to the user.

SUMMARY OF THE INVENTION

The sensor material of this invention is unique as it does not require skin preparation such as scrubbing or the presence of a gel for signal collection. The said sensor material can be used with or without direct contact with skin. This material offers unique performance characteristics such as it is elastic, flexible, soft, easy to melt process, and conductive. This sensor material can be processed by commercial melt processing techniques such as fiber spinning, sheet extrusion, injection molded, compression molding, etc. The availability of a choice of processing techniques leads to the option of several different sensor assemblies. For example, the material can be spun into fibers that can be woven into cloth to make clothing, sheets, arm bands, etc. The material can also be sheet extruded or injection molded into various shapes and sizes to fit more standard or conventional biopotential sensor assemblies.

This sensor material can be incorporated into a sensor system comprised of various modules that enable capturing biosignals, transforming them into a usable format and integrating them into a specific end application. Also, the sensor system of this invention is capable of measuring strain, moisture content etc. This gives our sensor the unique capability to be used as a single universal sensor used to measure multiple parameters used in diagnosis and monitoring using a sequential scan, for example, or to be used as a segmented sensor made out of the same material for parallel measurement of the aforementioned parameters.

The present invention relates to a sensor system which is comprised of three components including: (1) a sensor material, (2) a sensor form and (3) a signal capturing interface. This "sensor system" is used for capturing physiological signals, more specifically, the detection and measurement of bio-potentials expressed on the skin surface which arises from the activity of various organs such as heart, brain, nervous system, eyes, muscle etc. In addition to capturing bio-potential signals, other types of signals such as mechanical strain, moisture levels, temperature can be simultaneously detected using the sensor system.

The present invention includes a sensor system consisting of a sensor material consisting of a polymer/nano-composite compound. One specific example is a composite of a polymer and carbon nano-tubes. This material can be used to make gel-free/dry sensors without the need for any skin preparation. Also, this material can be used as a non-contact sensor (no direct contact with the skin), specifically used for signal detection and measurement (examples being biopotentials).

The sensor material can be fabricated into one of many forms, using virtually any plastics processing method, so that it can be incorporated into the users' environment. One specific example would be a sheet form used as a liner on mattresses or chair backs.

After being fabricated into a suitable form the sensor is attached to a signal capturing interface to capture, transmit and process the signals collected by the sensor material. One specific example is an embedded stranded wire that can be molded into the sheet form sensor to yield a signal sensor system which can be used as a 'sensor pad' by capturing signals by connecting to the wire.

An example of this sensor system would be a whole day vital signs monitoring system where the user does not have to wear a sensor (like conventional systems), but the sensor can be integrated into the day to day living/working environment of the user, more specifically, a bed liner or a seat back liner. The system can capture, process, transmit, receive, store and apply the data appropriately so the vital signs are captured throughout the day and stored and then relayed to the physician for analysis (FIG. 7).

The present invention more specifically reveals a multifunctional nano-composite sensor for detecting biologically generated electrical signals which is comprised of a polymeric composition having an electrically conductive wire embedded therein, wherein the polymeric composition has a dispersion phase and a dispersed phase, wherein the dispersion phase is comprised of a thermoplastic polymer or a thermoset polymer, wherein the dispersed phase includes an electrically conductive filler, wherein the polymeric composition is gel-free, and wherein the electrically conductive wire is adapted for conveying an electrical signal to a signal processing device.

The subject invention also reveals a method for monitoring the cardiovascular system of a patient for a prolonged period of time which comprises (1) the patient donning an article of clothing having integrated therein at least one multifunctional nano-composite sensor which is comprised of a polymeric composition having an electrically conductive sensor interface embedded therein, wherein the polymeric composition has a dispersion phase and a dispersed phase, wherein the dispersion phase is comprised of an elastomeric polymer matrix, wherein the dispersed phase includes at least one electrically conductive filler, and wherein the electrically conductive sensor interface is adapted for conveying an electrical signal to a signal processing device, (2) connecting the multifunctional nano-composite sensor to a signal processing device which is adapted for monitoring the cardiovascular system of a human being, and (3) monitoring the cardiovascular system of the patient.

The present invention further discloses a polymeric composition which is comprised of a thermoplastic polyurethane, a styrenic polymer, and at least one electrically conductive filler wherein the styrenic polymer is present in the composition at a level which is within the range of 10 weight percent to 50 weight percent and wherein the electrically conductive filler is present at a level which is within the range of 0.5 weight percent to 40 weight percent, based on the total weight of the polymeric composition.

BRIEF DESCRIPTION OF THE DRAWINGS

Various aspects of the present invention are illustrated by the accompanying drawings.

DETAILED DESCRIPTION OF THE INVENTION

Figure 1:
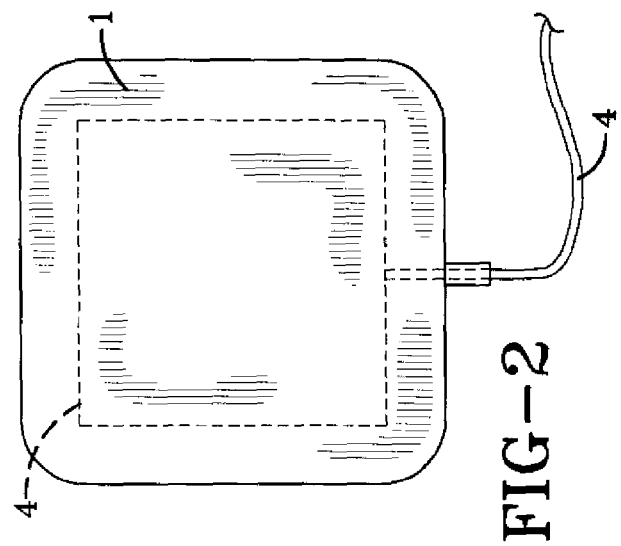
FIG. 1 illustrates a cross-sectional view of complete sensor which is made of a molded polymer nano-composite of this invention and which includes an embedded snap connector.

The polymer nano-composite used as a sensor material in accordance with this invention includes a dispersion phase and a dispersed phase. The dispersion phase is typically a thermoplastic polymer system and the dispersed phase is typically a functional nano and/or micro scale electrically conductive filler system.

The dispersion phase of the thermoplastic polymer system can be a single polymer or a blend/alloy. Typically, this thermoplastic polymer system will be chosen from the list of polymer systems such as: polyethylene, polypropylene, polyether block polyamides, polyester block co-polymers, styrenic block co-polymers, styrene based co and ter polymers (such as ABS, HIPS, ASA, SIBS, SEBS, SBS, etc), polyesters (such as PET, PTT, PETG, PBT), polycarbonates, polyphylene sulfide, polysulfones, thermoplastic elastomers, acrylate polymers (specifically ethylene methacrylate), thermoplastic urethanes and their blends/alloys thereof. Additionally the polymer system may contain polymeric modifiers and other additives.

The dicarboxylic acid which can be used in the hard polyesters that are useful in the practice of this invention are typically selected from the group consisting of terephthalic acid, isophthalic acid, naphthalenedicarboxylic acid, diphenyldicarboxylic acid or a mixture of 2 or more thereof. The diol used for the polyester is typically an alkylene glycol that contains 2-10 carbon atoms, 1,6-cyclohexanediol, 1,6-dimethanolcyclohexane or a mixture of two or more thereof. In general, it is preferred that a polyester having a more crystalline structure be used. These polyesters include poly (butylenes terephthalate) (PBT), poly (ethylene terephthalate) (PET), poly (trimethylene terephthalate) (PTT), poly (butylenes isophthalate) (PBI), poly (cyclohexylene-dimethylene terephthalate) (PCT), poly (ethylene naphthalate) (PEN), poly (trimethylene naphthalate) (PTN), and poly (butylenes naphthalate) (PBN).

The polyurethanes that are useful in the practice of this invention will typically consist of prepolymers and/or the thermoplastic polyurethanes (TPU) of the formula of $-R^1OCONHR^2-NHCOO-$) as hard segments, where $R^1$ is an alkylene group containing 2-6 carbon atoms and $R^2$ is an aromatic group, and the soft segments having polyalkylene oxide, polyester, polycaprolactone or a copolymer of two or more thereof. The preference is MDI-based polyether, polyester, polycaprolactone, ether-ester and ester-polycaprolactone TPU. The copolyester is polyether-polyester multiblock copolymer, where polyester is aromatic dicarboxylic acid incorporating with alkylene glycols having 2-6 carbon atoms. The preferred copolyester is using polytetrahydrofuran as soft segments and poly (butylenes terephthalate) as hard segments.

Another optional agreement is CBT®100, a low molecular weight thermoplastic resin of Cyclics Corporation, Schenectady N.Y. It is a blend of polybutylene terephthalate oligomers without a polymerization catalyst. It melts into a low viscosity liquid and is believed to not polymerize further into PBT.

To increase cold temperature impact characteristics it can be advantageous in one embodiment of this invention for the composition to contain a rubbery impact modifier composition component which could be one or more rubbery impact modifiers. The type of rubber impact modifier is a polymeric material which, at room temperature, is capable of recovering substantially in shape and size after removal of a force. However, the rubbery impact modifier should have a glass transition temperature of less than 0° C. Better performance normally attained when the glass transition temperature (Tg) is less than −5° C., −10° C., −15° C., with a Tg of less than −30° C. even better. The Lotader® resins from Arkema, Corporation (France) are some representative examples of such rubbery impact modifiers that can be included in one embodiment of this invention. These particular impact modifiers are functionalized polyolefin ethylene-acrylate terpolymers, such as ethylene-acrylic esters-maleic anhydride (MAH) or glycidyl methacrylate (GMA).

The rubbery impact modifier composition which can optionally be used is preferably a functionalized rubbery impact modifier and can be an ethylene copolymer that functions as a compatibilizing agent or surfactant, in that it forms a covalent bond and/or physical interaction with at least one polyester component and compatibly blends with the polyester component. In most cases, to get the high level of compatibility and physical properties, such as low temperature impact strength, a covalent bond will form between the polyester component and the functionalized rubbery impact modifier. The functionalized rubbery impact modifier component of the thermoplastic resin composition will normally represent from 2.0 weight percent to 50 weight percent of the composition, with 10 to 45 weight percent more preferable and 15 to 40 percent most preferable. The functionalized rubbery impact modifier is preferably present in the composition at a level which is within the range of 10 weight percent to 40 weight percent.

The functionalized rubbery impact modifier will often be a compatibilizing ethylene copolymer of the formula E/X/Y, where E is about 55-75%, X is about 15-35%, and Y is about 2-15% by weight of the compatibilizing ethylene copolymer, and E is ethylene.

X is an α,β-ethylenically unsaturated monomer derived from at least one of alkylacrylate, alkylmethacrylate, alkyl vinyl ether, carbon dioxide, sulfur dioxide, or mixtures thereof, where the alkyl groups contain 1-12 carbon atoms, such as vinyl acetate, methylacrylate, butylacrylate, and methyl vinyl ether. X can, for example, be a moiety derived from at least one of alkyl acrylate, alkyl methacrylate, alkyl vinyl ether, carbon monoxide, sulfur dioxide, or mixtures thereof. More specifically, X can, for example, contain up to about 35 weight percent of a moiety derived from at least one alkyl acrylate, alkyl methacrylate, or mixtures thereof where the alkyl groups contain 1-8 carbon atoms.

Y is an α,β-ethylenically unsaturated monomer containing a reactive group, such as epoxide, maleic anhydride, isocyanate, or oxazoline, for example. In one embodiment, Y is selected from the group consisting of glycidyl methacrylate and glycidyl acrylate, maleic anhydride, and isocyanato-ethylmethacrylate.

The functionalized rubbery polymer will typically contain repeat units that are derived from an acrylate monomer of the structural formula:

wherein R represents a hydrogen atom, an alkyl group containing from 1 to about 8 carbon atoms, or a moiety containing an epoxy group, and wherein $R^1$ represents a hydrogen atom or an alkyl group containing from 1 to about 8 carbon atoms. Some representative examples of monomers that can be used include methyl methacrylate, butyl acrylate, dimethylsiloxane. In many cases, R will represent an alkyl group containing from 1 to 4 carbon atoms. The moiety containing an epoxy group will typically be of the structural formula:

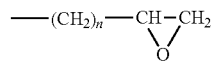

wherein n represents an integer from 1 to about 6. In most cases, n will represent 1. The functionalized rubbery polymer will generally also contain repeat units that are derived from a conjugated diolefin monomer, such as 1,3-butadiene or isoprene, a vinyl aromatic monomer, such as styrene or α-methyl styrene, a monoolefin monomer, such as ethylene or propylene, and/or a dialkylsiloxane monomer, such as dimethylsiloxane.

The functionalized rubbery polymer can optionally contain repeat units in its backbone which are derived from an anhydride group containing monomer, such as maleic anhydride. In another scenario, the functionalized rubbery polymer can contain anhydride moieties which are grafted onto the polymer in a post polymerization step.

In addition, reinforcing fibers and fillers may be incorporated into the thermoplastic elastomers according to the invention. The reinforcing fibers include those of glass, carbon, aromatic polyamide, and thermotropic liquid crystalline polymers. The fillers include talc, glass beads, calcium carbonate, carbon black, minerals, silicates and nano-fillers. Further, polyfluorocarbon compounds such as PTFE may be incorporated into the present elastomers, as well as pigments, thermal stabilizers, UV stabilizers, antioxidants, flame retardants and conductive materials (organic or/and inorganic). This invention is illustrated by the following examples that are merely for the purpose of illustration and are not to be regarded as limiting the scope of the invention or the manner in which it can be practiced. Unless specifically indicated otherwise, parts and percentages are given by weight.

Another class of rubbery impact modifiers is the olefins grafted with maleic anhydride. One example is polypropylene with 1% maleic anhydride, available as Polybond® 3200 from Crompton Corporation.

The dispersed phase primarily consists of a single or a mixture of nano and/or micro scale functional additive that are electrically conductive. These functional additives can be selected from the list: Carbon black powder, Multiwall Carbon nanotubes, single-wall carbon nanotubes, carbon fibers, carbon nanofibers, graphites, graphenes, graphite fibers, metal nanoparticles (gold, silver, tungsten, and copper nano particles), metal coated carbon fibers, metal or nano-particle coated organic and inorganic fillers and other conductive type fillers. The current invention uses a single functional filler or a combination of two or more fillers from the above list. In a typical example, the resulting composite sensor material of this invention, consists of, 0.1-35% loading of one or multiple conductive fillers as listed above.

TABLE 1

Conductivity of additives and their composite properties.

| Additives | Volume Resistivity | Properties of Composites |
| --- | --- | --- |
| Antistatic agents | ~$10^{11}$ Ω · cm | Isotropic shrinkage<br>Non-sloughing<br>Moderate elongation<br>Colorable<br>Transparent grade |
| Inherently dissipative polymers | ~$10^9$~$10^{12}$ Ω · cm | Isotropic shrinkage<br>Colorable<br>Moderate elongation |
| Inherently | ~$10^{-2}$~$10^0$ Ω · cm | Isotropic shrinkage |

TABLE 1-continued

Conductivity of additives and their composite properties.

| Additives | Volume Resistivity | Properties of Composites |
|---|---|---|
| conductive polymers | | Colorable |
| | | Moderate elongation |
| | | EMI/RFI shielding capability |
| Carbon black | ~$10^{-2}$ Ω · cm | Isotropic shrinkage |
| | | Strength/stiffness unchanged |
| | | Moderate elongation |
| | | Sloughing |
| | | High percolation threshold |
| | | EMI/RFI shielding capability |
| Carbon fiber | ~$10^{-3}$~$10^{-2}$ Ω · cm | Anisotropic shrinkage |
| | | Increase Strength/stiffness |
| | | Low elongation |
| | | Color option |
| | | Medium percolation threshold |
| | | EMI/RFI shielding capability |
| Stainless steel fiber | ~$10^{-5}$ Ω · cm | Isotropic shrinkage |
| | | Strength/stiffness unchanged |
| | | FDA compliant |
| | | Moderate elongation |
| | | EMI/RFI shielding capability |
| Nickel-coated graphite | ~$10^{-5}$ Ω · cm | Anisotropic shrinkage |
| | | Increase Strength/stiffness |
| | | Low percolation threshold |
| | | EMI/RFI shielding capability |

The carbon nanotubes used in making the thermoplastic polymer compositions of this invention normally have a diameter which is within the range of 5 to 20 nanometers and have a length which is within the range of 1 to 5 microns. The carbon nanotubes used in making the thermoplastic polymer composition of this invention more typically have a diameter which is within the range of 7 to 15 nanometers and have a length which is within the range of 1 to 3 microns. The carbon nanotubes used in making the thermoplastic polymer compositions of this invention preferably have a diameter which is within the range of 9 to 10 nanometers and have an aspect ratio which is within the range of 80 to 180 and more typically have an aspect ratio which is within the range of 90 to 150. The carbon nanotubes used in making the thermoplastic polymer composition of this invention preferably have an aspect ratio which is within the range of 95 to 120.

Specialty carbon nanotubes are also used in making the thermoplastic polymer compositions of this invention normally have a diameter which is within the range of 4 to 12 nanometers and have a length which is within the range of 1 to 5 microns. The specialty multiwall carbon nanotubes used in making the thermoplastic polymer composition of this invention more typically have a diameter which is within the range of 6 to 9 nanometers and have a length which is within the range of 1 to 3 microns. The specialty carbon nanotubes typically have 2 to 10 walls and more typically have 3 to 6 walls. The specialty carbon nanotubes used in making the thermoplastic polymer compositions of this invention typically has an aspect ratio of approximately 1,000.

Carbon black is one of the most popular fillers used in conductive polymers because of its low cost. Since its aspect ratio (ratio of length to diameter) is very small due to the particulate shape, and its percolation threshold is very high, the particles can be interconnected to be conductive. The conductive carbon black used in making the thermoplastic polymer compositions of this invention has an average particle size of 30 to 90 microns. More typically, the conductive carbon black used in making the thermoplastic polymer compositions of this invention has an average particle size of 40 to 60 microns.

A combination of various conductive fillers can have a synergistic effect on the conductivity of polymer composites. For example, the combination of graphite with regular carbon fiber had higher conductivity than any one of them with the same amount of loading. The combination of carbon black, regular carbon fiber, and graphite also has better EMI shielding effectiveness than any one of them or two of them. The synergistic effects have been also found from the incorporation of ICP (inherently conductive polymers) with conductive fibers.

In one embodiment of this invention the polymeric composition employed in making the sensors is comprised of a thermoplastic polyurethane, a styrenic polymer, and at least one electrically conductive filler wherein the styrenic polymer is present in the composition at a level which is within the range of 10 weight percent to 50 weight percent and wherein the electrically conductive filler is present at a level which is within the range of 0.5 weight percent to 40 weight percent, based on the total weight of the polymeric composition. In such compositions the styrenic polymer can be selected from the group consisting of styrene ethylene butadiene styrene block copolymers, styrene isoprene butadiene styrene block copolymers, styrene butadiene styrene block copolymers, styrene isoprene styrene block copolymers, or styrene ethylene propylene styrene block copolymers. The thermoplastic polyurethane polymer is typically a polyether based polyurethane elastomer. The electrically conductive filler is normally a mixture which is comprised of 0.5 weight percent to 10 weight percent carbon nanotubes and 1 weight percent to 20 weight percent carbon black, based on the total weight of the composition. It can be advantageous for the electrically conductive filler to be a mixture which is comprised of 0.5 weight percent to 10 weight percent multiwall carbon nanotubes and 1 weight percent to 20 weight percent carbon black, based on the total weight of the composition.

The above defined nano-composite can be prepared by using a co-rotating twin screw extruder; specifically a 25 mm diameter (D) twin-screw extruder of Berstorff, GmbH make was used. The components of the formulation were fed in two schemes; (i.) all from the throat of the extruder, passing it through a length of 44D and (ii.) the conductive filler only fed from the side-feeder, with the other components from the throat. The system is typically degassed by vacuum. A twin screw extruder can beneficially be utilized in processing the above defined nano-composite material. Pellets were collected by running the strands through a strand-pelletizer. Other melt blending/compounding techniques such as single screw extruders and banbury mixers can also be used.

Test Methods

The volume resistivity of a molded specimen is measured by direct-current (DC) resistance along the length direction around 40 mm at room temperature. The resistivity is converted to volume resistivity, $\rho_v$, as $\rho_v = WDR_v/L$, where W is the width, D the thickness, L the length of the specimen, and Rv is the measured resistance. The data will be the average of 10 specimens with standard deviation to the mean less than 5%.

Electrical conductivity is calculated by the following formula:

$$\sigma = \left( \frac{V}{I} \times \frac{\pi}{\ln 2} \times t \right)^{-1}$$

wherein σ is electrical conductivity, V, I and t are current, voltage, and thickness of the sample, respectively. It should be noted that the thickness is not much smaller than the distance between the probes so that electrical conductivity obtained is not real surface conductivity. The average conductivity of each specimen will be obtained from measurements at four different locations.

The thermal properties will be characterized by thermogravimetric analyzer (TGA), and differential scanning calorimetry, DSC. The mechanical properties (i.e. tensile strength, tensile modulus, elongation, toughness) will be test by Instron. The heat distortion temperature (HDT) is determined by HDT tester.

Sensor Forms

The polymer nano-composite sensor material can be converted into the required sensor form as per the design. The conversion methods are injection molding, fiber spinning, extrusion, or compression molding and combinations thereof. For injection molded sensors, an over-molding approach can be used in which the wire leads are pre-placed into the mold for attachment to the sensor. Alternatively, a predesigned sensor can be molded and then the wire leads are soldered or welded on the molded sensors. For extruded sensors, the composite can co-extruded along with the wire leads and then diced or cut into predesigned sensor forms. Alternatively, the polymer nano-composite can be extruded into a film or sheet or tape form or foam form and then the wire lead can be welded or soldered on top of it. Also the leads can be produced by metal deposition techniques on the composite film or a molded sensor. Alternatively, where the application warrants, metal snap connectors can be molded into the sheets by lamination, for an alternate method of connection. Alternatively the polymer nano-composite can be melt spun into fibers (filaments) and then woven into a fabric and clothing thereof. Either while making the sensor preforms (like sheets tapes etc.), or after the sensors are prepared, the surface that comes in contact with measuring medium, may be treated (by flame or other techniques) depending upon the requirement of the application.

The sensor 2 of FIG. 1 was made by laminating thin sheets of the polymeric material into the body 1 of the sensor 2 with a snap connector 3 being embedded therein. The sensor in FIG. 2 can be made by laminating thin sheets of polymeric material onto an electrically conductive wire 4 to embedded the electrically conductive wire into the body 1 of the sensor 2.

Figure 3:
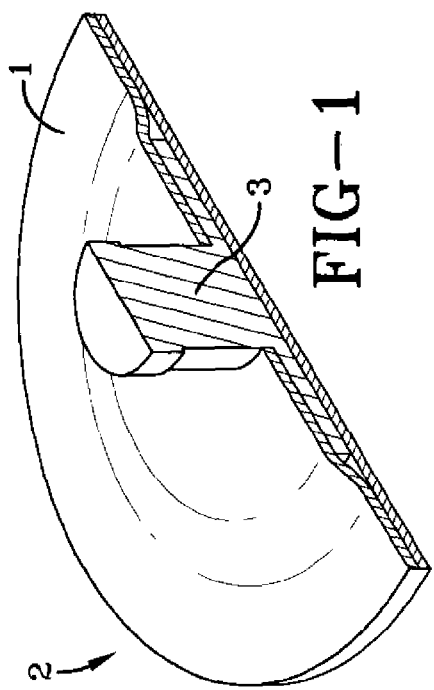
FIG. 3 is an exploded view illustrating a sensor interface having pin contacts piercing a sensor sheet to collect multiple bio-signal data.
Figure 4:
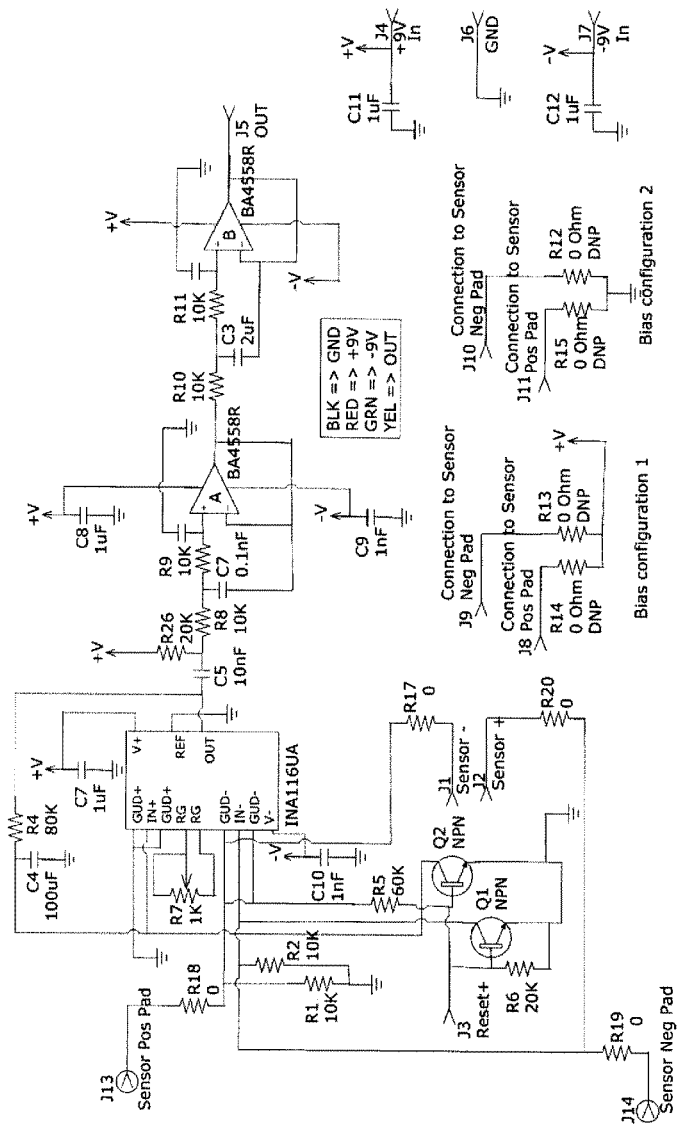
FIG. 4 shows the circuit utilized in the sensor interface illustrated in FIG. 3.
Figure 5:
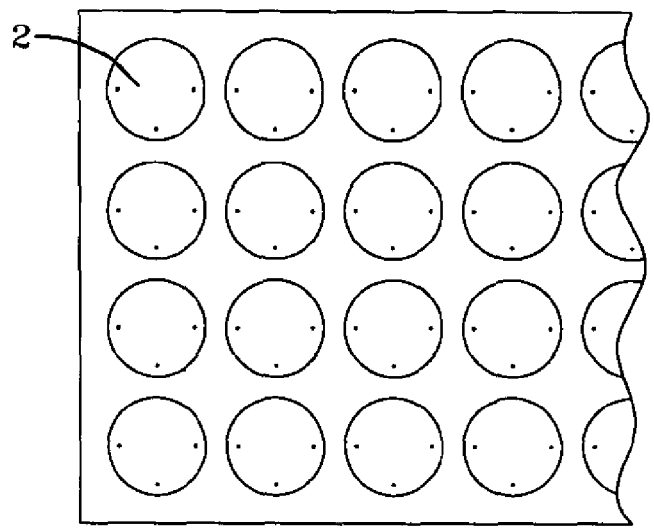
FIG. 5 illustrates a general schematic of a grid of sensor modules in a sensor system.
Figure 6:
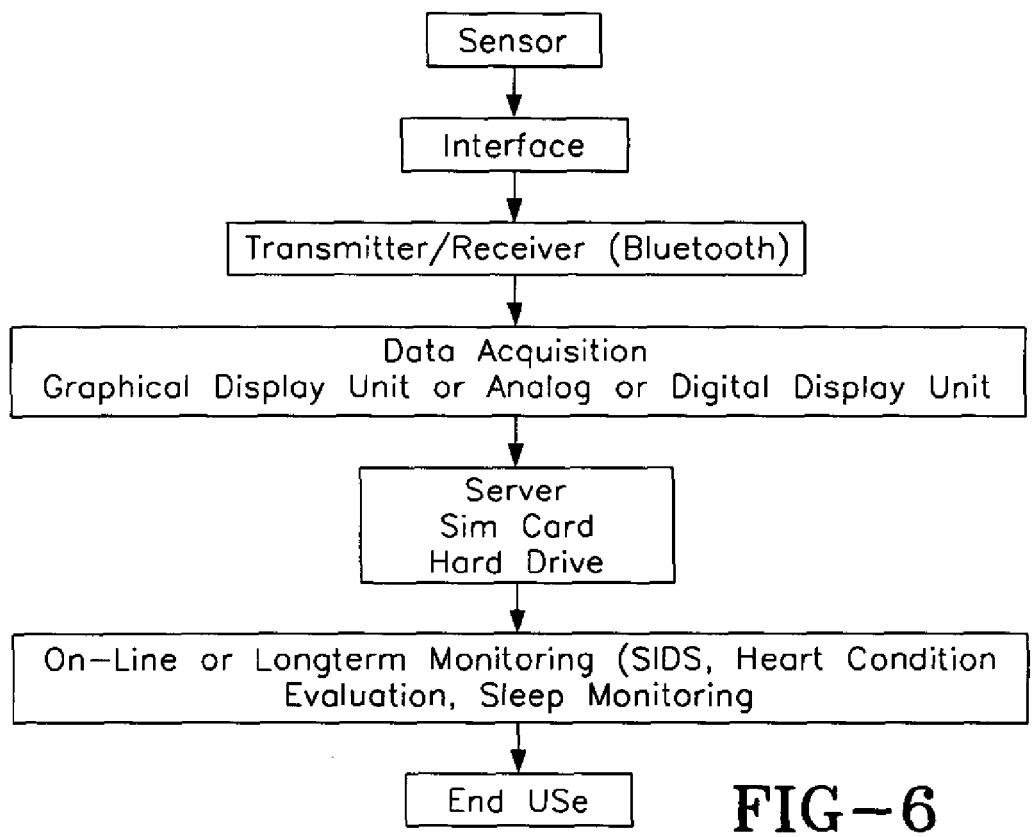
FIG. 6 is a schematic drawing showing the flow of data through interconnected modules in the sensor system for bio-signal capturing, processing, transmission, and monitoring.
Figure 7:
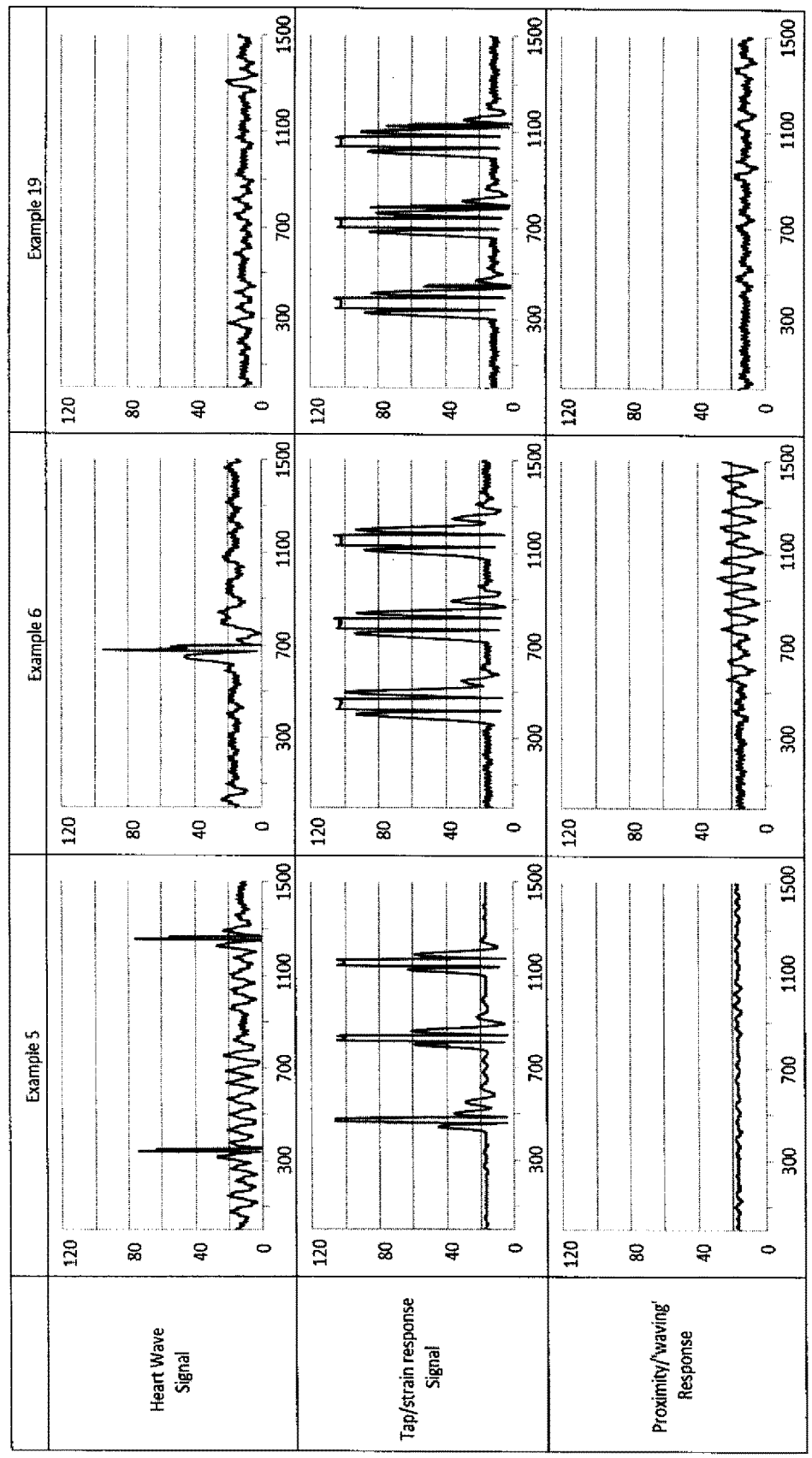
FIG. 7 illustrates multiple signal data collected from the sensor interface.

FIG. 3 is an exploded view illustrating a sensor interface having pin contacts piercing a sensor sheet to collect multiple bio-signal data. The sensor body 1 is in contact with interface pins 5 with are in electrical communication with a circuit board 6 having connecting wires 7 which are in further electrical communication with a sensor system module 8.

Figure 8:
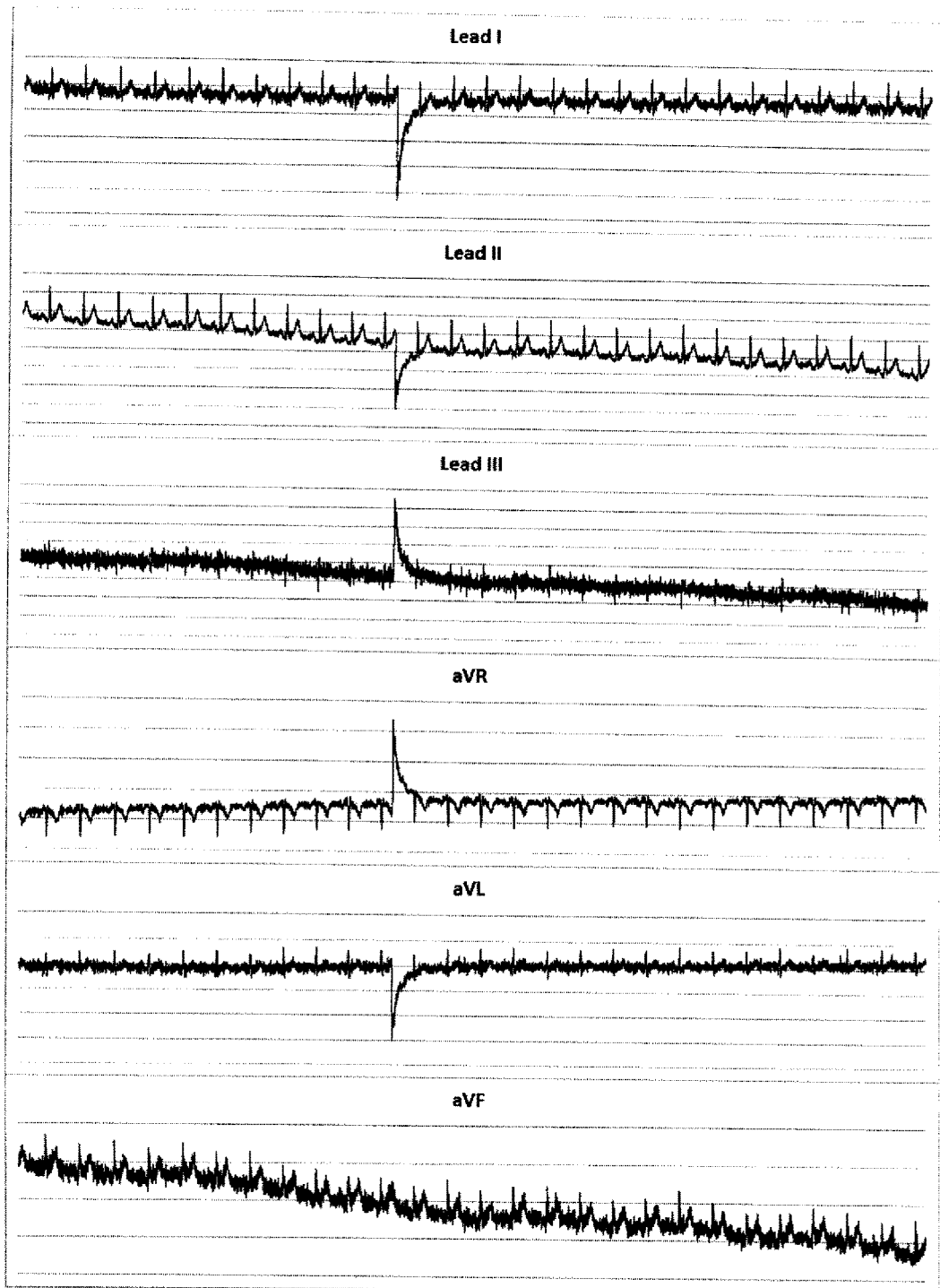
FIGS. 8 and 8A illustrate 12 lead ECG data.
Figure 8A:
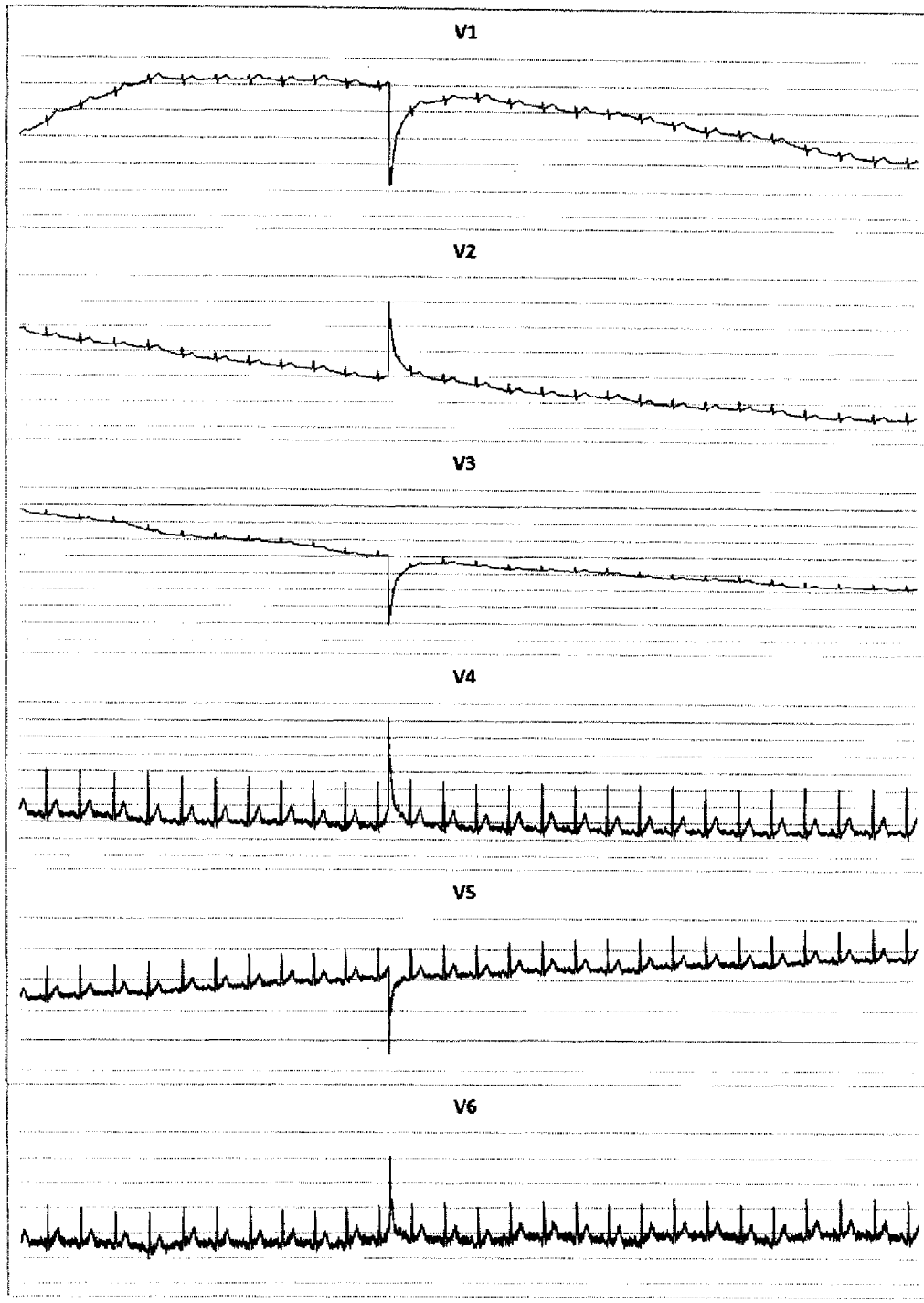
Figure 9:
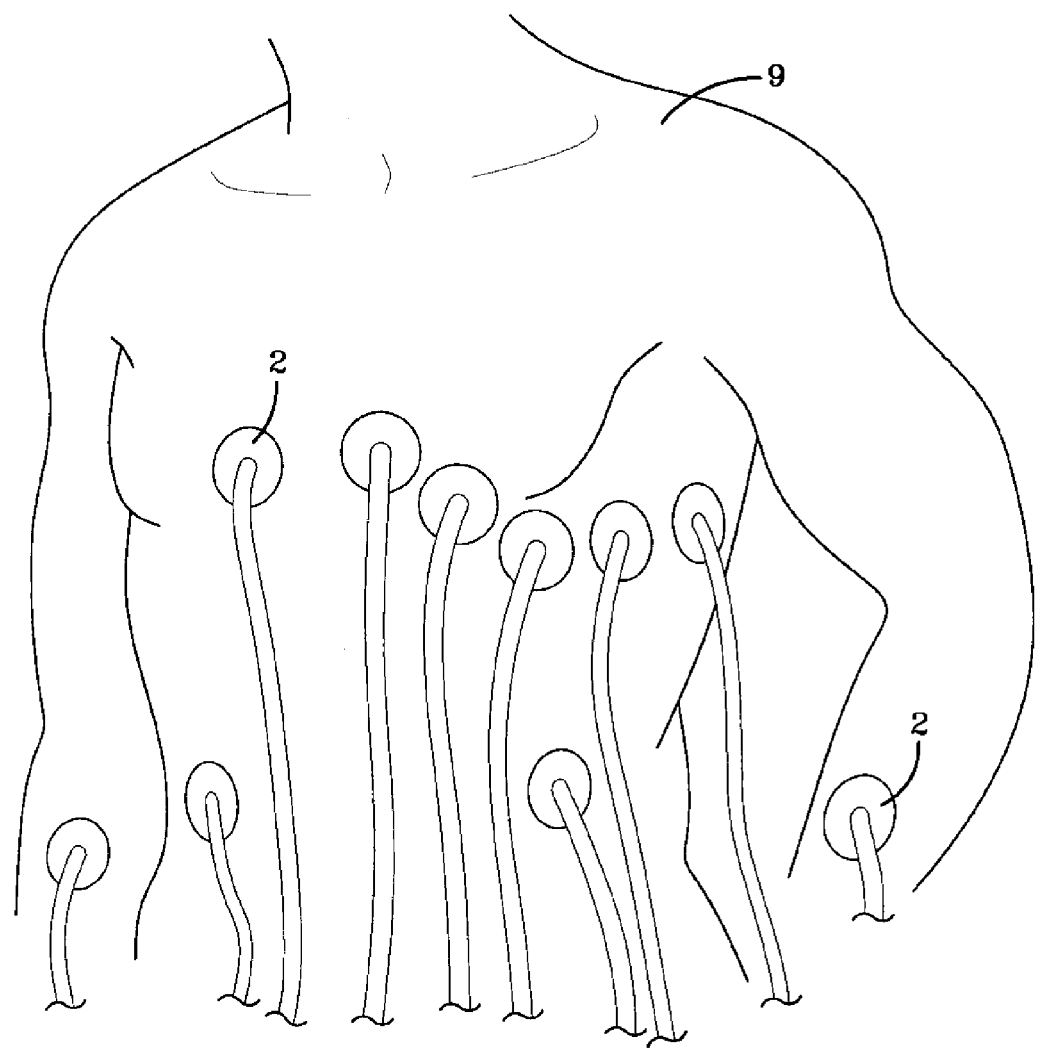
FIG. 9 illustrates a plurality of sensors with are in contact with a human subject for monitoring the cardiovascular system of the human subject.

FIGS. 8 and 8A show 12 lead ECG data which can be collected using the sensors of this invention. FIG. 9 illustrates a plurality of sensors 2 with are in contact with a human subject 9 for monitoring the cardiovascular system of the human subject.

This invention is illustrated by the following examples that are merely for the purpose of illustration and are not to be regarded as limiting the scope of the invention or the manner in which it can be practiced. Unless specifically indicated otherwise, parts and percentages are given by weight and the polymerizations were conducted in a reactor of the type depicted in FIGS. 1-5.

EXAMPLES

In this series of experiments, set of polymeric compositions were prepared and evaluated as materials for utilization in making sensors for detecting biosignals. The individual component materials utilized in making these polymeric compositions are identified in Table 2 as follows:

TABLE 2

Description of the material ingredients used.

| MATERIAL | SUPPLIER | GRADE | SPECIFICATIONS |
|---|---|---|---|
| ABS | CHI MEI Corporation | Polyac PA757 | General purpose acrylonitrile butadiene styrene. Melt flow rate = 1.8 g/10 min. |
| EMA | ExxonMobil Chemical | Optema ™ TC120 | Ethylene methyl acrylate copolymer intended for extrusion coating, coextrusion coating and extrusion lamination. Melt flow rate = 6 g/10 min. |
| Hytrel | DuPont | Hytrel ® 4069 | Low modulus grade with a nominal hardness of 40D and melt flow of 8.5 g/10 min. |
| LLDPE | Westlake | LF2018AB | Linear low density polyethylene with a melt flow rate = 0.8 g/10 min and density = 0.924. Ideal for sheet and tubing. |
| Pebax | Arkema | Pebax MH1637 | Polyether block amides, plasticizer-free, thermoplastic elastomers |
| PP | ExxonMobil Chemical | ExxonMobil ™ PP3155 | A homopolymer resin designed for spunbond nonwovens. Particularly suited for excellent spinning for uniform, high quality fabrics. Melt flow rate = 36 g/10 min. |
| PETG | SK Chemicals | Skygreen ® S2008 | General purpose polyethylene terephthalate glycol. |
| Thermoplastic Elastomer | Kaneka Corporation | Sibstar ® 073T | Thermoplastic elastomer with a shore hardness = 45A and melt flow rate = 7 g/10 min. |

TABLE 2-continued

Description of the material ingredients used.

| MATERIAL | SUPPLIER | GRADE | SPECIFICATIONS |
| --- | --- | --- | --- |
| Thermoplastic Elastomer | Kaneka Corporation | Sibstar ® 103T | Thermoplastic elastomer with a shore hardness = 46A and a melt flow rate = 0.10 g/10 min. |
| TPU | Merquinsa | PearlThane ® 11T93 | A polycaprolactone copolyester based thermoplastic polyurethane with a shore hardness = 93A. |
| TPU | Merquinsa | PearlThane ® 15N70 | A polyether copolymer-based thermoplastic polyurethane with a shore hardness = 72A. |
| TPU | Merquinsa | PearlThane ® D15N80 | A polyether-based thermoplastic polyurethane with a shore hardness = 81A. |
| CBT | Cyclics Corporation | CBT 100 | Melts to water-like viscosity when heated, then polymerizes into the engineering thermoplastic polybutylene terephthalate. |
| Modifier | Polyram Ram-On Industries | Bondyram ® 6000 | Maleic anhydride modified ABS. Compatibilizer and coupling agent for styrene compounds with a mass flow rate of 8 g/10 min. |
| Modifier | Arkema | Lotader ® 4700 | A random terpolymer of ethylene, acrylic ester and maleic anhydride with a melt flow rate = 7 g/10 min. |
| Modifier | Arkema | Lotader ® 8900 | A random terpolymer of ethylene, acrylic ester and glycidyl metacrylate with a melt flow rate = 6 g/10 min. |
| Coupling Agent | Chemtura | Polybond ® 3200 | Maleic anhydride modified homopolymers polypropylene used as a coupling agent. |
| Modifier | Kraton Polymers LLC | Kraton ® FG 1901G | A linear triblock copolymer based on styrene and ethylene/butylene with a polystyrene content of 30%. Melt flow rate = 14-28 g/10 min and shore hardness = 71A. |
| Lubricant | Harwick Standard | Stan-Lube 6056 Mineral | Processing oil lubricant |
| Additive | Wacker Silicones | Genoplast ® Pellet S | Silicone based performance additive |
| Siloxane | Multibase, A Dow Corning Company | Siloxane Masterbatch MB50-001 | Masterbatch consisting of 50% ultra-high molecular weight siloxane polymer dispersed in polypropylene homopolymer. |
| Antioxidant | HM Royal | Ethanox ® 310 | Tin-free antioxidant |
| Antioxidant | Maroon Chemical | Sunox 626 | Phosphate antioxidant |
| Antioxidant | Amfine | AO-412S | High molecular weight thioether antioxidant |
| Coupling Agent | Kenrich Petrochemicals | Kenrich ® Capow L38 | Titanate coupling agent |
| Modifier | Clariant Corporation | Licocene ® PE 4351 | Maleic-anhydride-modified polyethylene |
| Carbon Black | Cabot Corporation | Volcan ® XC-72 | High surface area conductive carbon black |
| Carbon Nanotubes | Akrema | Graphistrength ™ C100 | Multi-walled carbon nanotubes with a mean number of walls = 5-15, outer mean diameter = 10-15 nm, and length = 0.1-10 μm. |
| Carbon Nanotubes | Bayer Materials | Baytubes ® 150HP | Multi-walled carbon nanotubes with a mean number of walls = 3-15, outer mean diameter = 13-16 nm, and length = 1->10 μm. |
| Carbon Nanotubes | Cnano Technology Limited | Flotubes ™ 9000 | Multi-walled carbon nanotubes with an average diameter = 11 nm, and an average length = 10 μm. |
| Carbon Nanotubes | NANOCYL S. A. | Nanocyl ™ NC 7000 | Multi-walled carbon nanotubes with an aspect ratio >150. |

TABLE 2-continued

Description of the material ingredients used.

| MATERIAL | SUPPLIER | GRADE | SPECIFICATIONS |
|---|---|---|---|
| Carbon Nanotubes | SouthWest NanoTechnologies | SWeNT ® SMW-100 | Specialty Multiwalled carbon nanotbues with a mean number of walls = 3-6, a mean diameter = 6.6 nm, and an aspect ratio ~1,000. |

Tables 3-8 list the resin compositions (experiments 1-28). The compositions were made by combining the listed ingredients in the following manner which is non-limiting. In this series of experiments two of the ingredients were first mixed together and then re-extruded with a third ingredient. For example, a carbon black composition was made first and then carbon nanotubes were added in a second extrusion step. In this series of experiments a wide variety of modifications were made to both the manufacturing process and combination order to prepare the series of compositions.

In the procedure normally used compositions were made by reactive extrusion to make engineering thermoplastics. This was normally done by adding a dry blend mixture of the polymers, modifiers, stabilizers, processing aids, and fillers as a single feed into the feed hopper of a twin screw extruder with controlled specific energy input via control of feed rate (15 to 95% torque), RPM (60 to 900 rpm), process temperature and residence time distribution. The specific energy input was typically within the range of 0.2 to 0.4 kilowatt hours per kilogram and was more commonly within the range of 0.25 to 0.35 kilowatt hours per kilogram. It should be noted that some compositions can be prepared employing other suitable mixing devices for melt blending, such as a single screw extruder or a multiple single screw extruders or similar mixing devices.

In one of the procedures used the polymer nano-composite sensor material was made by charging the main feeder of a Berstorff ZE-25 twin screw extruder (L/D=44) with the ingredients identified in Tables 3-8. In one of the procedures used, a polymer nano-composite sensor material was compounded by a reactive blending/extrusion process using split-feed technology, wherein in a twin screw extruder (extruder length of 36D to 52D, wherein D is the diameter of the extruder screw), the select ingredient (mainly dispersion polymeric resin or mixture of resins thereof) was premixed and charged from the main feeder and the dispersed phase functional additives were introduced into the melt at a downstream feed port location at a distance of 8D to 30D, from the main feed throat of the extruder.

The operating conditions for the reactive extrusions used a screw speed of 200 to 600 RPM, a temperature profile of 30-45° C. (feed), 150-230° C. (Zone 2), 160-255° C. (Zone 3), 160-260° C. (Zone 4), 170-260° C. (Zone 5), 170-260° C. (Zone 6), 170-260° C. (Zone 7), 160-255° C. (Zone 8), and 160-255° C. (die). The product was pelletized and dried between 80-120° C. for 2-4 hours to a moisture content of less than 0.05% by weight. Then, test specimens were made by injection molding and were allowed to condition at a temperature of 23° C. for at least 24 hours before testing. The composition of the sensor materials made for evaluation are identified in Tables 3-8. The electrical and mechanical properties of these sensor materials are listed in Table 9 (experiments 1-28).

TABLE 3

Sensor material compositions

| MATERIALS | EXPERIMENT | | | | |
|---|---|---|---|---|---|
| | 1 | 2 | 3 | 4 | 5 |
| Polyace PA757 | 64.50 | 55.35 | 59.20 | — | — |
| Optema ™ TC120 | — | 11.40 | 10.00 | 92.00 | 88.00 |
| PearlThane ® 11T93 | 10.00 | — | — | — | — |
| CBT 100 | 5.00 | 5.50 | 5.00 | — | — |
| Bondyram ® 6000 | 5.00 | 4.50 | 5.00 | — | — |
| Stan-Lube 6056 Mineral | 0.50 | 0.45 | 0.50 | — | — |
| Siloxane Masterbatch MB50-001 | — | 4.50 | 5.00 | — | — |
| Ethanox 310 | — | 0.15 | 0.15 | — | — |
| A0-412S | — | 0.15 | 0.15 | — | — |
| Graphistrength ™ C100 | 15.00 | — | — | 8.00 | 12.00 |
| Baytubes ® 150HP | — | — | 15.00 | — | — |
| Nanocyl ™ NC 7000 | — | 18.00 | — | — | — |
| Total | 100 | 100 | 100 | 100 | 100 |

TABLE 4

Sensor material compositions

| MATERIALS | EXPERIMENT | | | | |
|---|---|---|---|---|---|
| | 6 | 7 | 8 | 9 | 10 |
| Optema ™ TC120 | 82.60 | 88.00 | 88.00 | 75.00 | 88.00 |
| Lotader ® 8900 | 1.00 | — | — | — | — |
| Kenrich ® Capow L38 | 0.40 | — | — | — | — |
| Licocene ® PE 4351 | 1.00 | — | — | — | — |
| Volcan ® XC-72 | — | — | 12.00 | 25.00 | 6.00 |
| Graphistrength ™ C100 | 15.00 | — | — | — | 6.00 |
| SWeNT ® SMW-100 | — | 12.00 | — | — | — |
| Total | 100 | 100 | 100 | 100 | 100 |

TABLE 5

Sensor material compositions

| MATERIALS | EXPERIMENT | | | | |
|---|---|---|---|---|---|
| | 11 | 12 | 13 | 14 | 15 |
| Optema ™ TC120 | 79 | 69 | — | — | — |
| Hytrel ® 4069 | — | — | 91 | — | — |
| Westlake LF2018AB | — | — | — | 91 | — |
| Pebax MH1637 | — | — | — | — | — |
| ExxonMobil ™ PP3155 | — | — | — | — | 90 |
| Lotader ® 4700 | — | — | — | 1 | — |
| Lotader ® 8900 | — | — | 1 | — | — |
| Polybond ® 3200 | — | — | — | — | 2 |
| Volcan ® XC-72 | 18 | 25 | — | — | — |
| Graphistrength ™ C100 | 3 | 6 | — | — | — |
| SWeNT ® SMW-100 | — | — | 8 | 8 | 8 |
| Total | 100 | 100 | 100 | 100 | 100 |

TABLE 6

Sensor material compositions

| MATERIALS | EXPERIMENT | | | | |
|---|---|---|---|---|---|
| | 16 | 17 | 18 | 19 | 20 |
| Sibstar ® 103T | 80 | 76 | 92 | — | — |
| PearlThane ® 15N70 | — | — | — | 92 | — |
| PearlThane ® 16N80 | — | — | — | — | 88 |
| Lotader ® 8900 | — | — | — | 2 | — |
| Kraton ® FG 1901G | 2 | 3 | 2 | — | — |
| Volcan ® XC-72 | 18 | 18 | — | — | 12 |
| Flotubes ™ 9000 | — | 3 | 6 | 6 | — |
| Total | 100 | 100 | 100 | 100 | 100 |

TABLE 7

Sensor material compositions

| MATERIALS | EXPERIMENT | | | | |
|---|---|---|---|---|---|
| | 21 | 22 | 23 | 24 | 25 |
| Sibstar ® 073T | — | — | — | — | 45 |
| PearlThane ® 15N70 | — | — | — | — | 47.1 |
| PearlThane ® 16N80 | 88 | 80 | 77 | 92 | — |
| Lotader ® 8900 | — | 2 | 2 | 2 | 1.5 |
| Sunox 626 | — | — | — | — | 0.2 |
| Ethanox ® 310 | — | — | — | — | 0.2 |
| Volcan ® XC-72 | — | 18 | 18 | — | — |
| Graphistrength ™ C100 | 12 | — | 3 | 6 | — |
| Flotubes ™ 9000 | — | — | — | — | 6 |
| Total | 100 | 100 | 100 | 100 | 100 |

TABLE 8

Sensor material compositions

| MATERIALS | EXPERIMENT | | |
|---|---|---|---|
| | 26 | 27 | 28 |
| Optema ™ TC120 | — | — | 6.3 |
| Pebax MH1637 | — | — | 39.69 |
| ExxonMobil ™ PP3155 | — | — | — |
| Skygreen ® S2008 | — | — | 30 |
| Sibstar ® 073T | 37.5 | 44.1 | — |
| PearlThane ® 15N70 | 38.65 | 46.158 | — |
| CBT 100 | — | — | 3.15 |
| Lotader ® 8900 | 2.25 | 1.47 | 2.89 |
| Kraton ® FG 1901G | — | — | 4.15 |
| Sunox 626 | 0.3 | 0.196 | — |
| Ethanox ® 310 | 0.3 | 0.196 | — |
| Stan-Lube 6056 Mineral | — | — | 0.32 |
| Genioplast ® Pellet S | — | — | 3.2 |
| Volcan ® XC-72 | 18 | 2 | — |
| Graphistrength ™ C100 | — | — | 10.3 |
| Flotubes ™ 9000 | 3 | 5.88 | — |
| Total | 100 | 100 | 100 |

TABLE 9

Electrical and Mechanical properties of the sensor materials compositions made in this series of experiments.

| Exp. # | RESISTANCE | | | | | TENSILE | | | | |
|---|---|---|---|---|---|---|---|---|---|---|
| | Strand (Ω/sq) | Surface Plaque (Ω/sq) | Volume Plaque (Ω/sq) | Surface Sheet (Ω/sq) | Volume Sheet (Ω/sq) | Modulus (MPa) | Stress at Yield (MPa) | Stress at Break (MPa) | Strain at Break (%) | Density |
| 1 | 4.00E+01 | 1.12E+05 | — | — | — | 2707.2 | 41.3 | 41.3 | 2.0 | 1.1240 |
| 2 | 2.40E+01 | 3.10E+03 | — | — | — | 2046.3 | 21.7 | 21.8 | 1.4 | 1.1047 |
| 3 | 8.00E+11 | 1.26E+10 | — | — | — | 1889.9 | 24.8 | 24.8 | 2.0 | 1.0930 |
| 4 | 7.70E+06 | 3.00E+10 | 1.10E+11 | 1.90E+05 | 4.80E+04 | 48.1 | 8.4 | 8.1 | 197.9 | 0.9587 |
| 5 | 2.30E+03 | 2.00E+05 | 3.80E+05 | 5.40E+03 | 5.20E+03 | 61.4 | 8.7 | 8.4 | 158.6 | 0.9870 |
| 6 | 9.20E+01 | — | — | — | — | — | — | — | — | — |
| 7 | 5.90E+03 | 1.00E+06 | 1.60E+06 | 5.10E+03 | 6.50E+03 | 60.9 | 9.0 | 8.8 | 94.5 | 0.9973 |
| 8 | 8.40E+07 | 1.90E+13 | 2.00E+13 | 1.60E+06 | 1.20E+07 | 41.5 | 8.2 | 8.0 | 306.3 | 0.9963 |
| 9 | 7.00E+02 | 4.10E+03 | 6.20E+03 | 2.00E+03 | 2.60E+03 | 66.2 | 9.8 | 9.6 | 231.0 | 1.0473 |
| 10 | 1.30E+05 | 4.00E+10 | 1.10E+11 | 1.00E+06 | 4.00E+05 | 53.8 | 8.5 | 8.2 | 198.4 | 0.9940 |
| 11 | 8.30E+03 | 3.60E+03 | 4.30E+03 | 6.60E+02 | 1.00E+03 | 77.3 | 9.0 | 8.8 | 185.7 | 1.0393 |
| 12 | 1.20E+02 | 1.70E+03 | 7.80E+02 | 2.60E+02 | 2.30E+02 | 114.0 | 10.6 | 10.3 | 129.4 | 1.0950 |
| 13 | — | 3.90E+03 | 2.30E+03 | 6.60E+03 | 6.70E+03 | 109.7 | 13.9 | 13.8 | 69.2 | 1.1450 |
| 14 | — | 7.30E+03 | 7.50E+03 | 1.70E+03 | 2.90E+03 | 595.5 | 18.4 | 16.0 | 57.4 | 0.9703 |
| 15 | — | 4.50E+03 | 4.90E+03 | 8.20E+02 | 2.70E+03 | 2261.0 | 38.4 | 38.1 | 5.4 | 0.9447 |
| 16 | 1.40E+05 | 6.00E+03 | 4.30E+03 | 1.90E+05 | 1.80E+06 | 34.4 | 14.2 | 14.0 | 320.7 | 1.0400 |
| 17 | 2.50E+02 | 4.10E+03 | 5.00E+03 | 8.40E+03 | 1.20E+04 | 65.5 | 13.8 | 13.5 | 265.8 | 1.0590 |
| 18 | 1.60E+08 | 1.40E+11 | 1.60E+11 | 1.80E+07 | 1.10E+07 | 29.0 | 11.7 | 11.7 | 299.1 | 0.8727 |
| 19 | 1.20E+04 | 5.50E+05 | 5.20E+05 | 1.00E+04 | 1.30E+04 | 21.2 | 6.9 | 9.9 | 261.9 | 1.1197 |
| 20 | 1.40E+06 | 5.20E+10 | 5.70E+10 | 1.60E+04 | 1.40E+04 | 32.5 | 11.4 | 12.4 | 584.9 | 1.1507 |
| 21 | 1.50E+02 | 1.40E+04 | 1.20E+04 | 6.00E+03 | 2.20E+05 | 75.1 | 6.5 | 6.3 | 44.8 | 1.1433 |
| 22 | 1.30E+04 | 1.70E+05 | 1.10E+05 | 1.30E+04 | 1.20E+04 | 45.7 | 6.2 | 6.2 | 157.0 | 1.1747 |
| 23 | 5.50E+02 | 1.60E+03 | 1.10E+03 | 1.20E+03 | 1.20E+03 | 67.1 | 7.1 | 7.1 | 65.9 | 1.1933 |
| 24 | 5.70E+01 | 2.50E+02 | 1.70E+03 | 2.90E+02 | 3.20E+02 | 68.3 | 6.7 | 6.5 | 37.1 | 1.2083 |
| 25 | 9.30E+03 | 3.10E+03 | 5.40E+03 | 2.10E+03 | 2.90E+03 | 21.4 | 3.8 | 3.7 | 153.7 | 1.0540 |
| 26 | 4.80E+03 | 1.20E+03 | 3.70E+03 | 8.70E+02 | 9.30E+02 | 31.0 | 3.6 | 3.6 | 124.7 | 1.0850 |
| 27 | 9.10E+03 | 9.10E+03 | 6.90E+03 | 3.30E+03 | 3.30E+03 | 20.3 | 3.6 | 3.5 | 140.3 | 1.0360 |
| 28 | 2.10E+04 | 2.40E+04 | — | — | — | 198.7 | 9.1 | 9.1 | 8.0 | — |

As can be seen from Table 9, many of the sensor material compositions made were determined to be highly electrically conductive making them excellent candidates as materials for utilization in manufacturing biosensors. Additionally, many of these compositions also exhibited good mechanical properties which would allow them to be employed in commercial manufacturing of biosensors. These sensor material compositions were subsequently further evaluated to determine their ability to capture biosignals, including both electrical and mechanical signals.

Biosignal Measurement Set-Up

Figure 2:
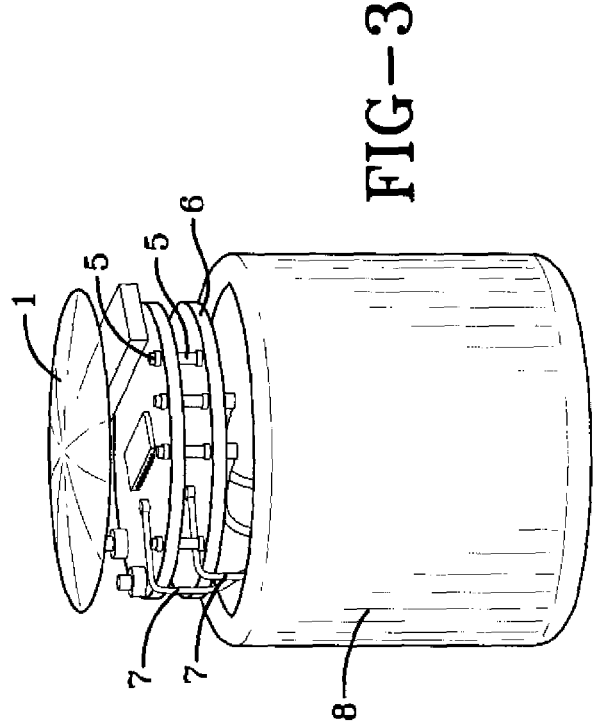
FIG. 2 illustrates a complete sensor which is made with a molded polymer nano-composite of this invention wherein the complete sensor has a copper wire embedded therein.
Figure 10D:
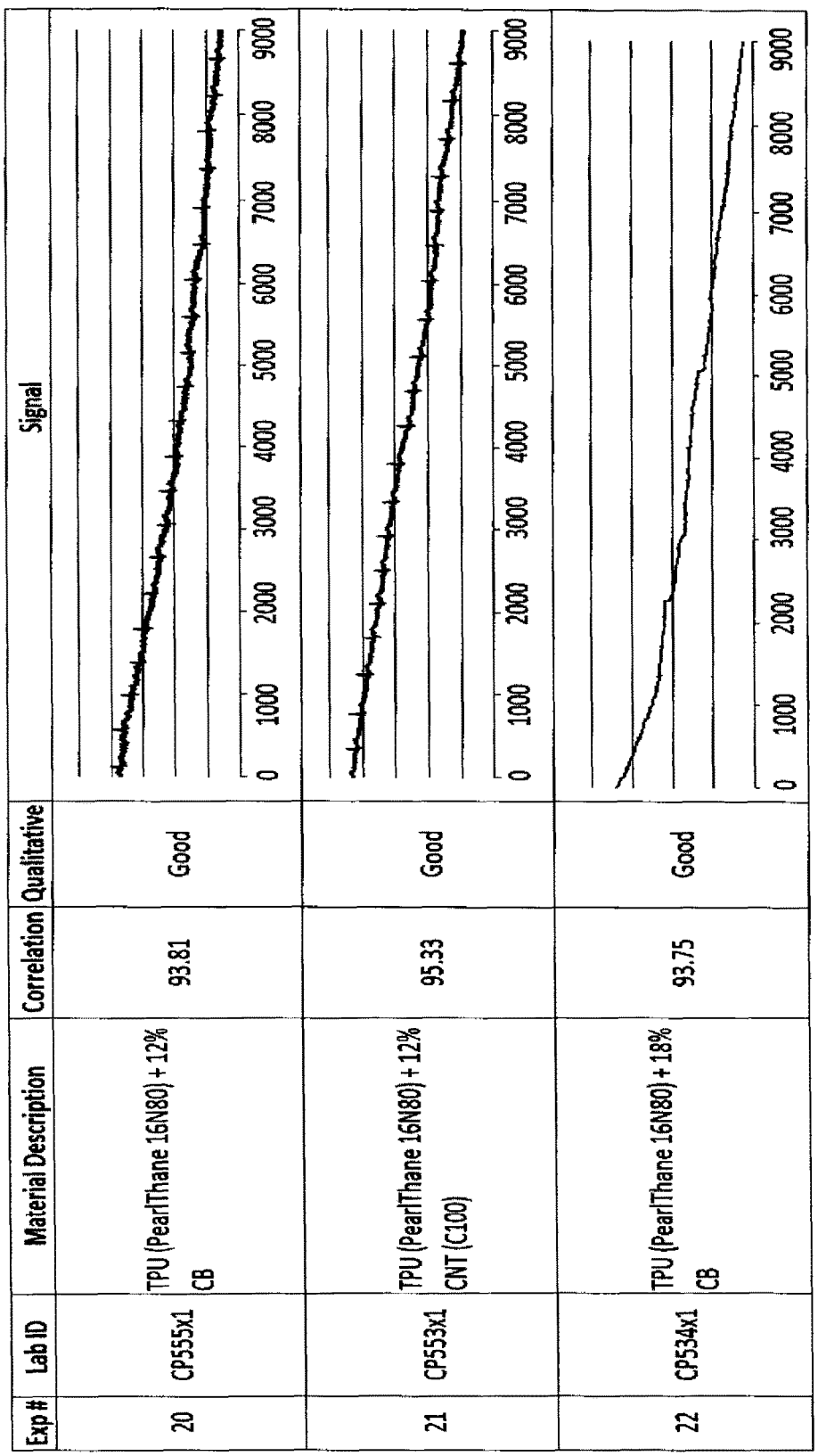
FIGS. 10-10F illustrate the bio-signal data collected in Examples 4-27.

Two types of evaluation were conducted. The first method used a multi-functional signal capturing interface wherein a sensor testing prototype was used to test the ability of the sensor material (in sheet-form) to acquire multiple signals using just a single interface as shown in FIG. 1 and FIG. 2. The body 1 of the sensor 2 can have a snap connector 3 embedded therein as illustrated in FIG. 1. This interface can utilize pin connectors to pierce the sensor material sheet or can have an electrically conductive wire 4 embedded into the body 1 of the sensor as shown in FIG. 2. The signal collected by the pin connector interface was fed to an instrumentation amplifier and was then processed through a Sallen-Key bandpass filtering stage. The resultant heart-wave signal was then digitized and plotted using a USB interface and a graphical-user-interface program. The data values from the digitized wave-form were captured and displayed. This system was used to capture ECG/heart-wave signals, strain signals, and proximity signals as shown in FIG. 10.

The second method used a ECG Front-End Performance Demonstration Kit (ADS1298ECG-FE) made by Texas Instruments, in conjunction with shielded interface cables and a computer for data collection and analysis of the ECG signals (FIG. 10) captured by the sensor materials fabricated into the form of an electrode.

When ECG signals were measured with each electrode made using the sensor materials described in Tables 3-8, another ECG signal was simultaneously measured using a standard electrode from Vermed Corporation. Both sets of data were collected at 500 samples/sec and 10,000 data samples were recorded. A simple high pass filter was applied to both sets of data to remove frequencies below 5 Hz to give baseline-drift-free signals. A simple differentiator was then used to detect the position of each R peak in the Vermed electrode signal, and these R peak time stamps were used to separate the signals into individual "heartbeats", each of which was 400 data points long (200 points each to the left and right of the R peak time stamp). Cross correlation was then performed for each heartbeat of the sensor data with its corresponding heartbeat of the Vermed electrode data. For cross correlation, data for each pair of heart beats were normalized to have a peak amplitude of 1, and a sliding inner product of the sensor data was computed as a function of a time lag applied to the Vermed electrode data, as shown in the following equation for correlation calculation:

$$R(l) = \Sigma \text{Sensor data}(n) \cdot \text{Vermed data}(n-l) \quad l = 0, \pm 1, \pm 2, \ldots$$

The correlation value is expressed as a percentage of unity. The values for each of the material examples are presented in FIGS. 10-10F.

As can be seen from FIG. 10, many of electrodes made from the sensor materials evaluated captured ECG signals of excellent signal quality which are comparable to conventional dry electrodes with the advantage of not requiring a wet conductive gel. The sensors of this invention also offer the advantage of not requiring any skin preparation procedure and the resulting skin irritation associated therewith. The sensors of this invention are also highly conformable which makes them more comfortable for human subjects. Under conditions of prolonged exposure the sensors of this invention further offer the additional advantage of not causing skin irritation.

While certain representative embodiments and details have been shown for the purpose of illustrating the subject invention, it will be apparent to those skilled in this art that various changes and modifications can be made therein without departing from the scope of the subject invention.

What is claimed is:

1. A multi-functional nano-composite sensor for detecting biologically generated electrical signals in the absence of conductive gels which is comprised of a polymeric composition having an electrically conductive sensor interface embedded therein, wherein the polymeric composition has a dispersion phase and a dispersed phase, wherein the dispersion phase is comprised of an elastomeric polymer matrix which is comprised of a polyester based thermoplastic polyurethane and a styrenic polymer, wherein the dispersed phase includes at least one electrically conductive filler, and wherein the electrically conductive sensor interface is adapted for conveying an electrical signal to a signal processing device, wherein the styrenic polymer is present in the composition at a level which is within the range of 10 weight percent to 50 weight percent and wherein the electrically conductive filler is present at a level which is within the range of 0.5 weight percent to 40 weight percent, based on the total weight of the polymeric composition.

2. The multi-functional nano-composite sensor as specified in claim 1 wherein the sensor is adapted for detecting and measuring bio-signals from a human body.

3. The multi-functional nano-composite sensor as specified in claim 1 wherein the sensor is integrated into a woven fabric, a non-woven fabric, a foam structure, a sheet, or a fiber.

4. The multi-functional nano-composite sensor as specified in claim 2 wherein the sensor is integrated into a chair, a bed, an article of clothing or a handgrip.

5. The multi-functional nano-composite sensor as specified in claim 1 wherein the electrically conductive filler is selected from the group consisting of multiwall carbon nanotubes, single wall carbon nanotubes, single multiwall nanotubes, carbon nanofibers, graphenes, metal nanoparticles, metal coated carbon fibers, and metal coated organic fillers, metal coated inorganic fillers, nano-particle coated organic fillers, and nano-particle coated inorganic fillers.

6. The multi-functional nano-composite sensor as specified in claim 5 wherein the metal nanoparticle is selected from the group consisting of gold nanoparticles, silver nanoparticles, tungsten nanoparticles, and copper nanoparticles.

7. The multi-functional nano-composite sensor as specified in claim 5 wherein the electrically conductive filler is selected from the group consisting of metal decorated multiwall carbon nanotubes, metal decorated single wall carbon nanotubes, metal decorated single multiwall nanotubes, metal decorated carbon nanofibers, and metal decorated graphenes.

8. The multi-functional nano-composite sensor as specified in claim 5 wherein the electrically conductive filler is present in the composition at a level of 3 weight percent to 20 weight percent based on the total weight of the composition.

9. The multi-functional nano-composite sensor as specified in claim 5 wherein the electrically conductive filler is a mixture which is comprised of 0.5 weight percent to 10 weight percent multiwall carbon nanotubes and 1 weight percent to 20 weight percent carbon black, based on the total weight of the composition.

10. The multi-functional nano-composite sensor as specified in claim 1 wherein the conductive sensor interface is selected from the group consisting of an electrically conductive wire, an electrically conductive snap connector, and an electrically conductive pin.

11. The multi-functional nano-composite sensor as specified in claim 1 wherein the styrenic polymer is selected from the group consisting of styrene ethylene butadiene styrene block copolymers, styrene isoprene butadiene styrene block copolymers, styrene butadiene styrene block copolymers, styrene isoprene styrene block copolymers, and styrene ethylene propylene styrene block copolymers.

12. The multi-functional nano-composite sensor as specified in claim 1 wherein the electrically conductive filler is a mixture which is comprised of 0.5 weight percent to 10 weight percent carbon nanotubes and 1 weight percent to 20 weight percent carbon black, based on the total weight of the composition.

13. The multi-functional nano-composite sensor as specified in claim 1 wherein the electrically conductive filler is a mixture of carbon nanotubes and at least one conductive additive selected from the group consisting of carbon black powder, carbon fibers, carbon nanofibers, graphites, graphite fibers, metal nanoparticles, metal coated carbon fibers, and metal or nano-particle coated organic and inorganic fillers.

14. A sensor system which is comprised of the multi-functional nano-composite sensor as specified in claim 10 and a signal processing device including an electronic circuit which is in electrical communication with at least one electrical component selected from the group consisting of an electronic circuit consisting of amplifiers, filters and capacitors, or an embedded micro-processor that uses a form of the aforesaid electronic components.

15. The sensor system as specified in claim 14 which is further comprised of at least one module for bio-signal capturing, processing, transmission, reception, data acquisition, storage and processing for an end-use application.

16. A method for monitoring the cardiovascular system of a patient for a prolonged period of time which comprises (1) the patient donning an article of clothing having integrated therein at least one multifunctional nano-composite sensor as specified in claim 1, (2) connecting the multifunctional nano-composite sensor to a signal processing device which is adapted for monitoring the cardiovascular system of a human being, and (3) monitoring the cardiovascular system of the patient.

* * * * *